(12) United States Patent
La Pietra et al.

(10) Patent No.: US 10,064,604 B2
(45) Date of Patent: Sep. 4, 2018

(54) ULTRASOUND CALIBRATION FIXTURE

(71) Applicant: Carestream Health, Inc., Rochester, NY (US)

(72) Inventors: Lynn M. La Pietra, Rochester, NY (US); Michael R. Spaeth, Webster, NY (US)

(73) Assignee: Carestream Health, Inc., Rochester, NY (US)

( * ) Notice: Subject to any disclaimer, the term of this patent is extended or adjusted under 35 U.S.C. 154(b) by 0 days.

(21) Appl. No.: 15/200,735

(22) Filed: Jul. 1, 2016

(65) Prior Publication Data

US 2018/0000459 A1 Jan. 4, 2018

(51) Int. Cl.

| | |
|---|---|
| *F16M 11/00* | (2006.01) |
| *A61B 8/00* | (2006.01) |
| *F16B 1/00* | (2006.01) |
| *F16M 13/02* | (2006.01) |
| *F16B 2/22* | (2006.01) |
| *F16C 11/04* | (2006.01) |

(52) U.S. Cl.
CPC ............ *A61B 8/587* (2013.01); *A61B 8/4209* (2013.01); *F16B 1/00* (2013.01); *F16B 2/22* (2013.01); *F16C 11/04* (2013.01); *F16M 13/022* (2013.01); *F16B 2001/0028* (2013.01); *F16B 2001/0035* (2013.01)

(58) Field of Classification Search
CPC ....... F16M 11/041; F16M 13/02; F16M 13/00
USPC .......................... 248/316.1, 316.2, 74.1, 74.2
See application file for complete search history.

(56) References Cited

U.S. PATENT DOCUMENTS

| | | | |
|---|---|---|---|
| 5,230,339 A | 7/1993 | Charlebois | |
| 6,462,277 B1 * | 10/2002 | Young | H02G 3/185 174/66 |
| 8,357,853 B1 * | 1/2013 | Gretz | H02G 3/14 174/480 |
| D719,524 S * | 12/2014 | DeCosta | D13/155 |
| 9,192,355 B2 | 11/2015 | Smith et al. | |
| 9,282,945 B2 | 3/2016 | Smith et al. | |
| 2005/0218016 A1 * | 10/2005 | Garcia, Jr. | G11B 33/0444 206/308.1 |
| 2008/0115955 A1 * | 5/2008 | Gorin | H02G 3/22 174/66 |
| 2011/0275937 A1 | 11/2011 | Kumazawa | |
| 2014/0043933 A1 | 2/2014 | Belevich et al. | |

OTHER PUBLICATIONS

P-W Hsu, et al. "Real-time Freehand 3D Ultrasound Calibration," CUED/F-INFENG/TR 565, Sep. 2006, University of Cambridge, Department of Engineering, 14 pages.

(Continued)

*Primary Examiner* — Steven M Marsh (57) ABSTRACT

A fixture for securing a sonography transducer in place against a test surface of a phantom has a cap having a cap surface, wherein the cap is formed to seat against an edge of the phantom and to maintain spacing between the cap surface and the test surface. One or more cutouts in the cap surface are dimensioned to accept the sonography transducer. One or more flexible supports within or adjacent the one or more cutouts are configured to stabilize at least one side of the transducer within the cutout.

11 Claims, 10 Drawing Sheets

(56) References Cited

OTHER PUBLICATIONS

Sun Nuclear Corporation: Ultrasound QA Solutions, retrieved from Internet Dec. 8, 2017: URL:http:/snc4quarter.sunnuclear.net/documents/datasheets/gammex/ultrasound.pdf, 8 pages.
European Search Report dated Nov. 13, 2017 for European Patent Application No. 17 177 952.3, 2 pages.
Nuclear Corporation: Ultrasound QA Solutions, retrieved from Internet Dec. 8, 2017: URL:http:/snc4quarter.sunnuclear.net/documents/datasheets/gammex/ultrasound.pdf, 8 pages.

* cited by examiner

ULTRASOUND CALIBRATION FIXTURE

TECHNICAL FIELD

The invention relates generally to the field of medical ultrasound systems and methods, and in particular to an apparatus for supporting a transducer when used with a calibration phantom.

BACKGROUND

Ultrasound imaging systems are used to support examination and diagnosis of patients in a range of medical applications. Ultrasound utilizes sound waves at frequencies higher than those perceptible to the human ear. Ultrasonic images known as sonograms are generated as a result of pulsed ultrasonic energy that has been directed into tissue using a probe. The probe obtains echoed sound energy from the internal tissue and provides signal content that represents the different sound reflectivity exhibited by different tissue types. This signal content is then used to form images that visualize features of the internal tissue. Medical ultrasound, also known as diagnostic sonography or ultrasonography, is used as a diagnostic imaging technique used to help visualize features and operation of tendons, muscles, joints, vessels and internal organs of a patient.

Figure 1:
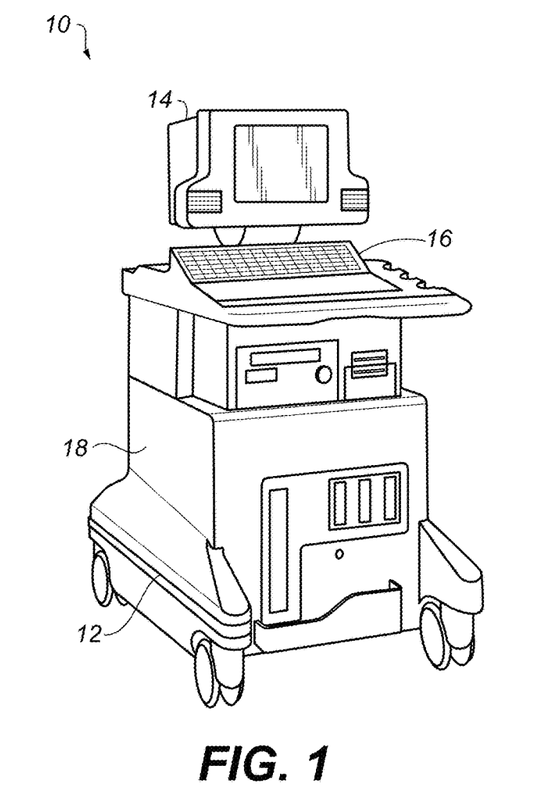
FIG. 1 shows an exemplary ultrasound system.

FIG. 1 shows an exemplary portable ultrasound system 10 that use a cart/base/support, cart 12, a display/monitor 14, one or more input interface devices 16 (such as keyboard or mouse), and a generator 18. The display 14 can also be a touch screen to function as an input device. As illustrated, the ultrasound system 10 can be a mobile or portable system designed to be wheeled from one location to another.

Like other types of imaging systems, ultrasound imaging equipment requires periodic calibration. Calibration procedures, carried out by a lead operator, field technician, or other qualified person, help to provide consistent results from the ultrasound system.

To assist in calibration of the ultrasound probe and system, a number of types of ultrasound phantom have been devised. Used to evaluate the performance of diagnostic ultrasound systems, these devices are configured with surfaces that are compatible with ultrasound probes and with internal features that allow ultrasound measurement over a range of relative densities and dimensions, mimicking the acoustic properties of human tissue and providing target structures with acoustic densities in a range that is encountered in anatomical examinations. Phantoms help to detect undesirable performance changes that can occur through normal use, compensating for factors such as aging and deterioration of ultrasound system components. Routine calibration can help to reduce the number of repeat examinations, the duration of examinations, and overall maintenance down-time, as well as helping to verify the effectiveness of maintenance actions. Phantoms are routinely employed for clinical Quality Assurance (QA), Preventative Maintenance, field service testing, research and development, manufacturing, teaching, and sales and marketing use.

The calibration sequence often requires the technician to simultaneously operate system controls and the keyboard console of an ultrasound system while manually maintaining the ultrasound probe in place along a particular portion of the phantom. This arrangement can become very awkward and physically straining, particularly where calibration techniques or their results may require more in-depth image acquisition and analysis. For portable systems such as those shown in FIG. 1, the calibration technician may have to perform calibration under adverse conditions, such as where space, lighting, and accessibility are limited.

Thus, it can be seen that a need exists for flexible tools to support ultrasound image calibration procedure.

SUMMARY

Certain embodiments described herein address the need for improved calibration tools for operating ultrasound apparatus. Embodiments of the present disclosure provide a calibration fixture that can be adapted for use with any of a number of standard, commercial ultrasound phantoms. The calibration fixture allows hands-free operation, so that a technician can maintain the probe in a fixed position during testing, without requiring the technician to hold the probe in place.

According to at least one aspect of the invention, there is described a fixture for securing a sonography transducer in place against a test surface of a phantom, the fixture comprising: a cap having a cap surface, wherein the cap is formed to seat against an edge of the phantom and to maintain spacing between the cap surface and the test surface; one or more cutouts in the cap surface dimensioned to accept the sonography transducer; and one or more flexible supports within or adjacent the one or more cutouts and configured to stabilize at least one side of the transducer within the cutout.

These aspects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DETAILED DESCRIPTION OF THE EMBODIMENTS

The following is a detailed description of embodiments of the invention, reference being made to the drawings in which the same reference numerals identify the same elements of structure in each of the several figures.

Where they are used in the context of the present disclosure, the terms "first", "second", and so on, do not necessarily denote any ordinal, sequential, or priority relation, but are simply used to more clearly distinguish one step, element, or set of elements from another, unless specified otherwise.

As used herein, the term "energizable" relates to a device or set of components that perform an indicated function upon receiving power and, optionally, upon receiving an enabling signal.

In the context of the present disclosure, the phrase "in signal communication" indicates that two or more devices and/or components are capable of communicating with each other via signals that travel over some type of signal path. Signal communication may be wired or wireless. The signals may be communication, power, data, or energy signals. The signal paths may include physical, electrical, magnetic, electromagnetic, optical, wired, and/or wireless connections between the first device and/or component and second device and/or component. The signal paths may also include additional devices and/or components between the first device and/or component and second device and/or component.

In the context of the present disclosure, the term "subject" is used to describe the patient that is undergoing ultrasound imaging. The terms "sonographer", "technician", "viewer", "operator", and "practitioner" are used to indicate the person who actively operates the sonography equipment.

Figure 2:
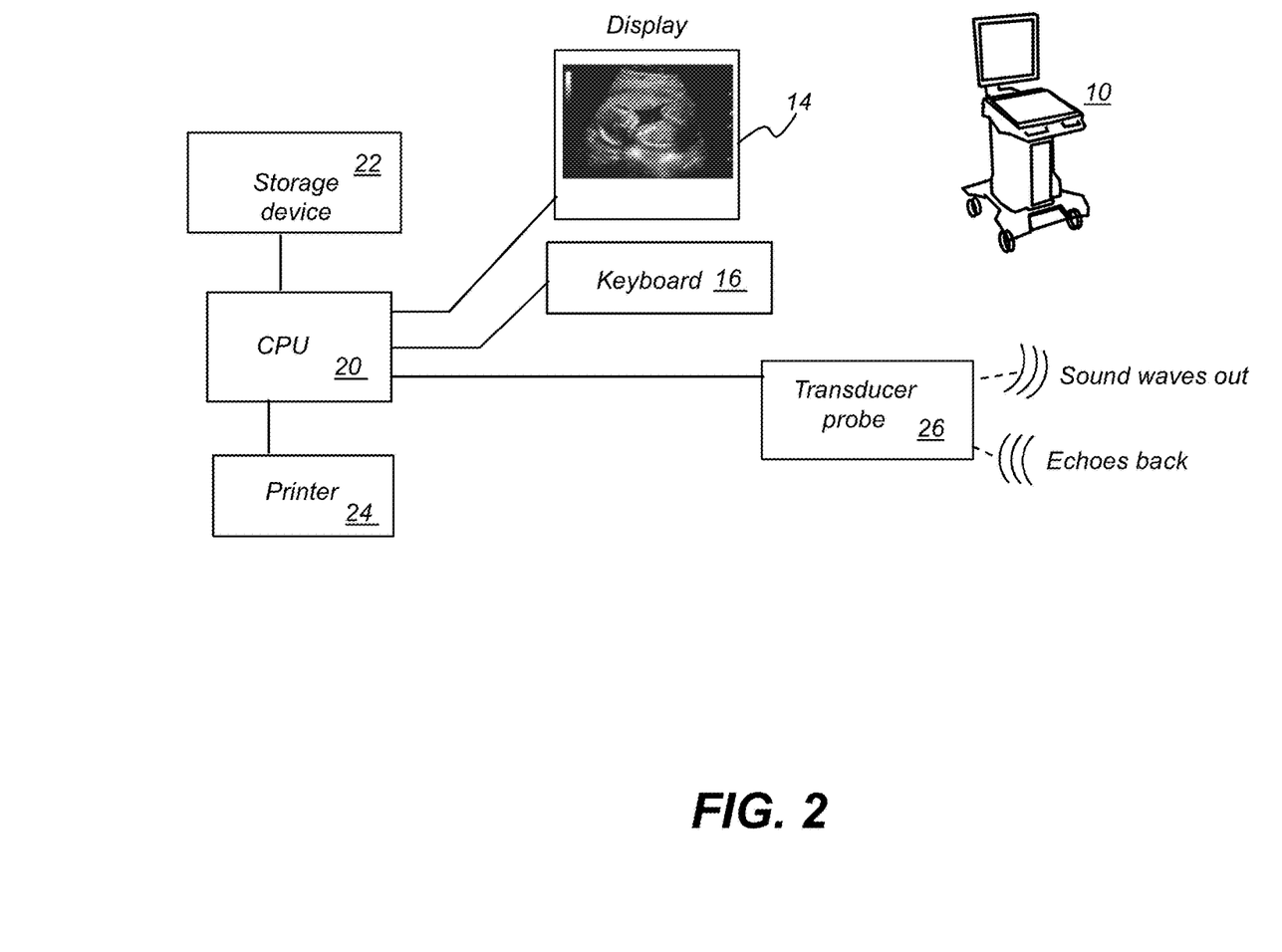
FIG. 2 shows a schematic of an exemplary ultrasound system.

As the schematic diagram of FIG. 2 shows, the ultrasound system 10 has a central processing unit CPU 20 that provides control signals and processing capabilities. CPU 20 is in signal communication with display 14 and interface device 16, as well as with a storage device 22 and an optional printer 24. A transducer probe 26 provides the ultrasound acoustic signal and generates an electronic feedback signal indicative of tissue characteristics from the echoed sound.

Figure 3:
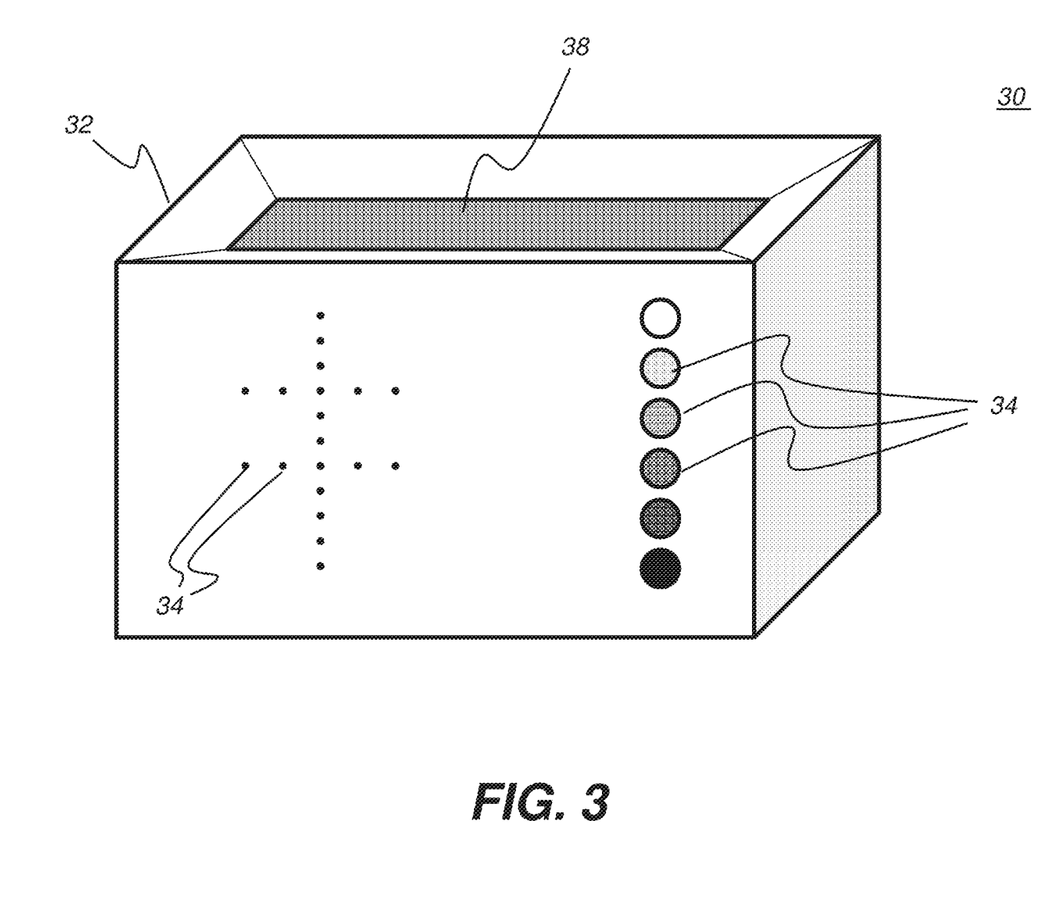
FIG. 3 is a perspective view that shows a conventional phantom that can be used for ultrasound and transducer calibration.

The perspective view of FIG. 3 shows a phantom 30 that can be used for ultrasound and transducer calibration. An exemplary phantom for ultrasound calibration is the Model 535H Basic QA Phantom from ATS Laboratories, Bridgeport, Conn., USA. A housing 32 provides a protective enclosure for phantom 30 components and has markings 34 that indicate relative locations of various internal structures built into phantom 30. One or more surfaces 38 are formed along sides of the phantom 30 to mimic qualities of skin tissue and serve as test surfaces for probe placement. The materials used typically allow the use of acoustic gels or other materials conventionally used to improve acoustic transmission at the skin surface.

Figure 4:
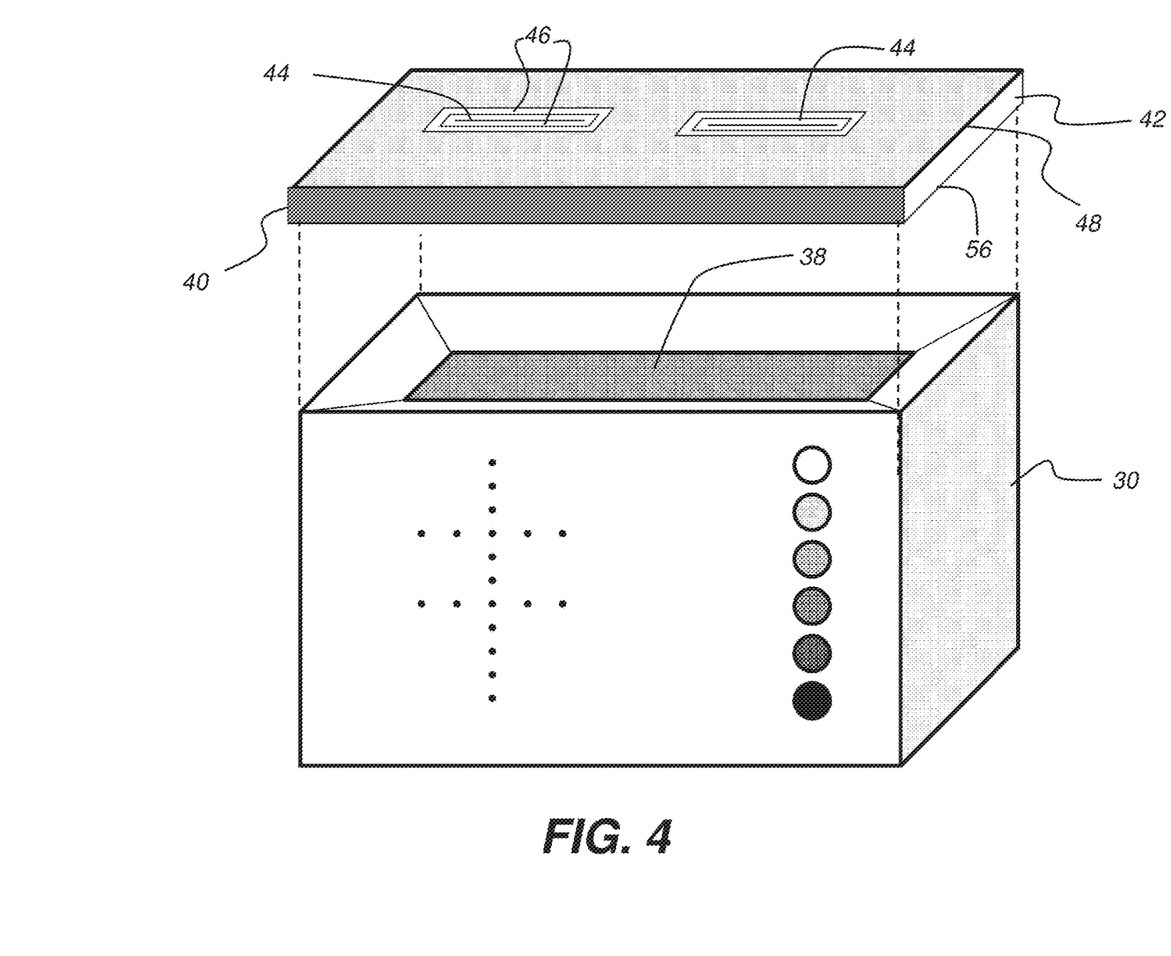
FIG. 4 is a perspective view that shows an embodiment with a calibration fixture formed as a cap that is featured to removably seat onto edges of a phantom.

The perspective view of FIG. 4 shows an embodiment with a calibration fixture 40 formed as a hood, covering, or cap 42 that is featured to removably seat onto and fit in place along an edge of phantom 30. Cap 42 can be formed from metal, plastic, composite, or other suitable materials or combination of materials. When cap 42 is seated in position, with sides 56 gripping against the corresponding side surfaces of the phantom, a cap surface 48 of calibration fixture 40 is positioned so that it is spaced apart from a test surface 38 of the phantom. One or more cutouts 44 are provided in cap 42, suitably dimensioned for temporary insertion of an ultrasound or sonography probe that is seated in contact with surface 38 during testing. One or more flexible supports 46 disposed within or adjacent to cutout 44 are configured to stabilize a side or sides of the probe transducer when inserted into the cutout.

Figure 5:
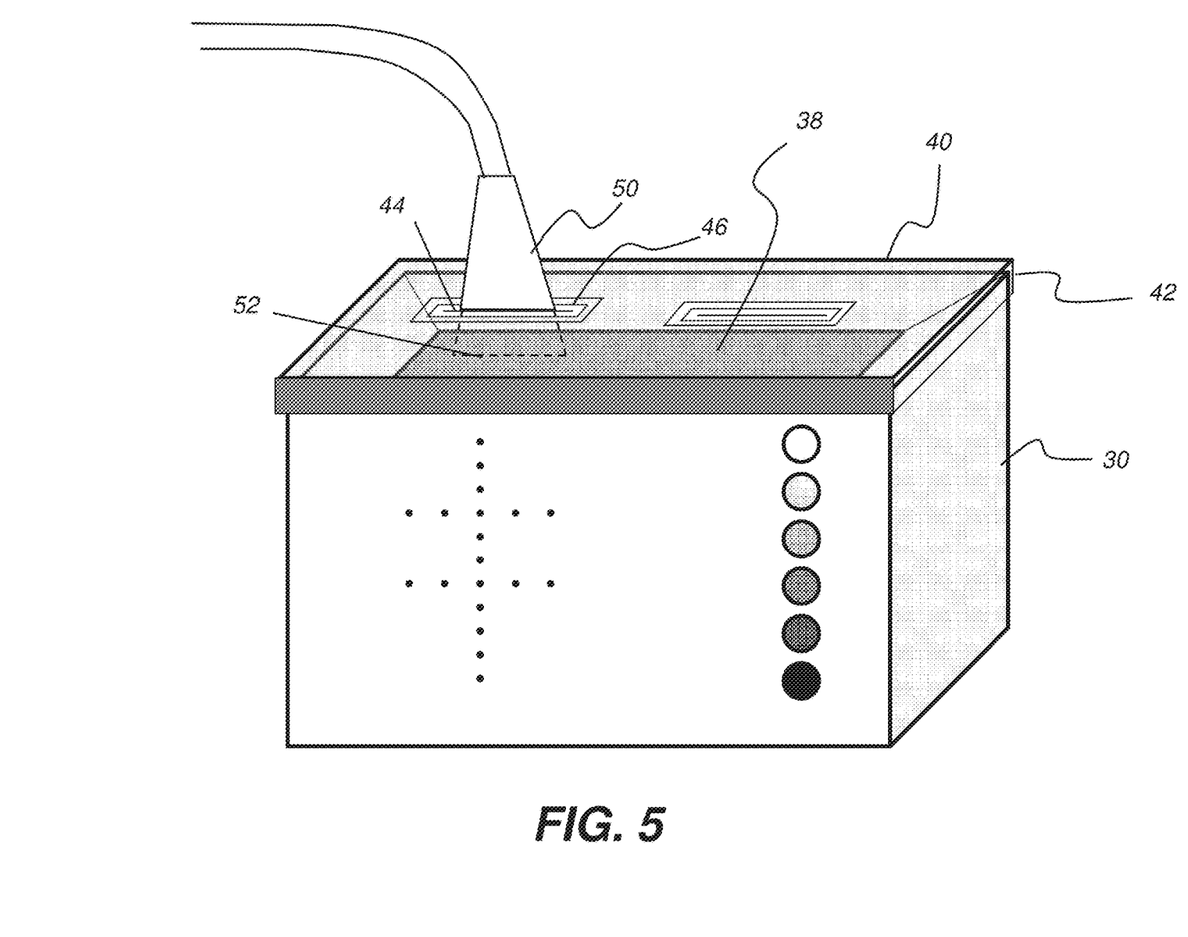
FIG. 5 is perspective view that shows a calibration fixture seated in place against an edge of the phantom.

FIG. 5 is perspective view that shows calibration fixture 40 seated in place against an edge of phantom 30. A sonography transducer 50 is inserted into cutout 44 and held in position so that it presses against test surface 38 of the phantom, stabilized and retained by flexible supports 46. When properly positioned, a sensing tip 52 of transducer 50 is in acoustical contact with surface 38, typically with the added use of an acoustic gel between the transducer 50 and surface 38, as described previously.

Figure 6:
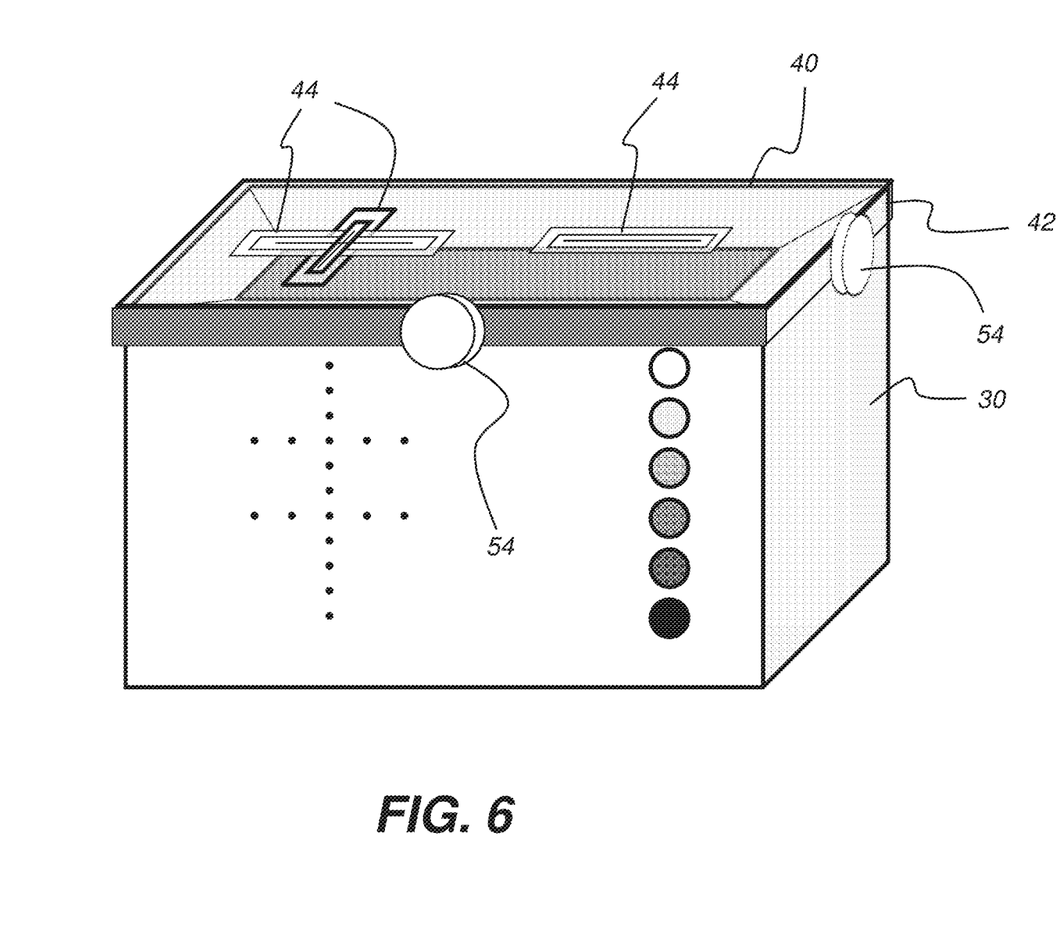
FIG. 6 is a perspective view that shows an alternate embodiment of a calibration fixture having a different configuration of cutouts, slotted to allow positioning of the probe at alternate angles.

FIG. 6 is a perspective view that shows an alternate embodiment of fixture 40 having a different configuration of cutouts 44, slotted to allow positioning of the transducer at alternate angles. Cutouts 44 can be provided in any suitable size or angular arrangement for testing. Alternately, a single cutout 44 can extend along a portion of cap 42, sufficient to allow the transducer 50 to be moved to different portions of the phantom as desired, for obtaining signals from alternative positions. One or more knobs 54 can be provided, allowing the technician to more tightly couple cap 42 of fixture 40 into position. Other features can alternately be used to provide fasteners for improved coupling of the fixture 40, including mechanical latches, clips, or hinges, magnetic elements, or hook and loop fasteners, such as VELCRO fasteners, for example.

Figure 7A:
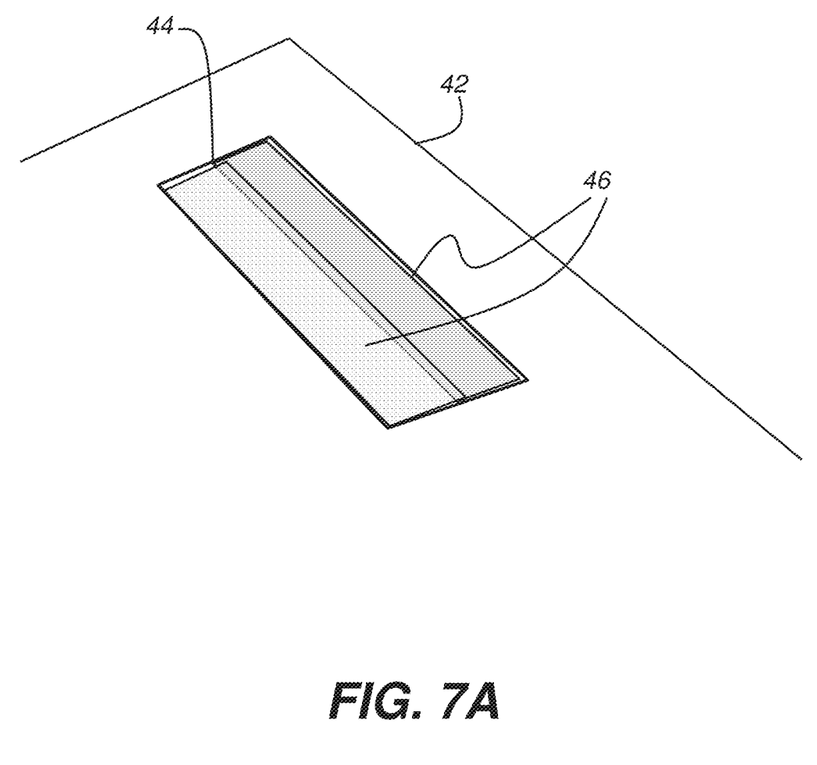
FIG. 7A is a perspective view that shows a portion of a cap with flexible supports arranged to slightly overlap each other over the cutout.

FIG. 7A is a perspective view that shows a portion of cap 42 with flexible supports 46 arranged to butt against or even slightly overlap each other over cutout 44. In the embodiment shown, supports 46 are formed as stiff but partially flexible rubber or plastic leaves, with sufficient compliance in bending to accept and hold the transducer probe in place without support from the operator/technician. In this arrangement, flexible supports 46 provide a type of slotted diaphragm for allowing transducer positioning and removal.

Figure 7B:
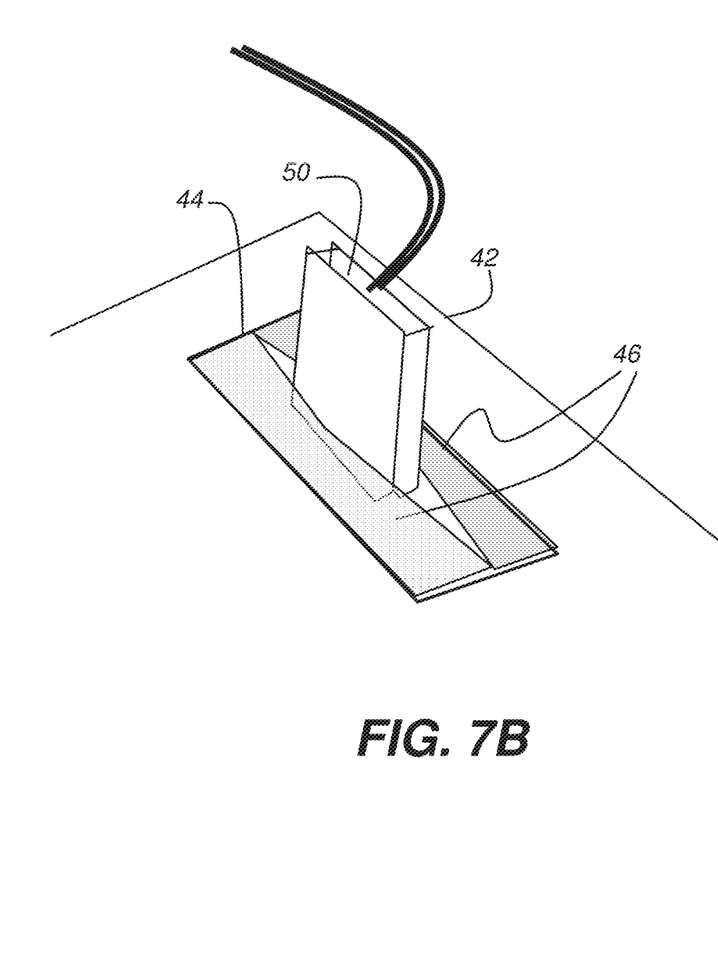
FIG. 7B is a perspective view that shows the flexible supports of FIG. 7A flexed to accept insertion of a probe.

FIG. 7B is a perspective view that shows the flexible supports 46 of FIG. 7A with flexure to accept insertion of a transducer. Some amount of stiffness for supports 46 allows stable support of transducer 50 in position within cutout 44.

Figure 8:
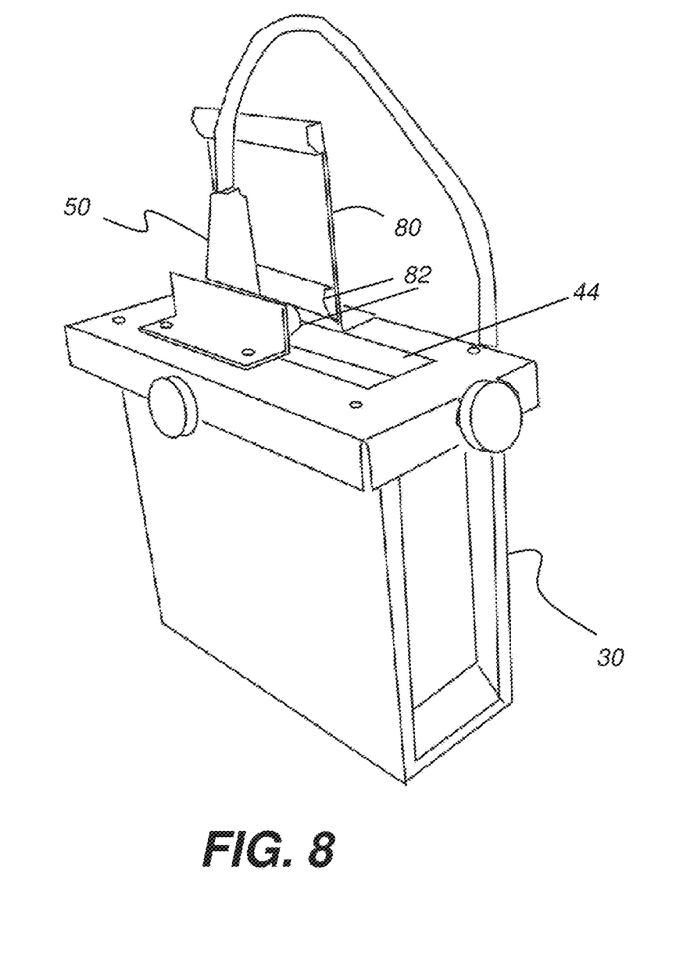
FIG. 8 is a perspective view that shows an embodiment that provides further support of the probe using a bracket.

FIG. 8 is a perspective view that shows an embodiment that provides further support of transducer 50 using a bracket 80 that extends outward from the cap 42. Opposing flexible couplers 82 cushion and secure transducer 50 in place within cutout 44. Couplers 82 can be of a flexible foam material, for example.

Figure 9:
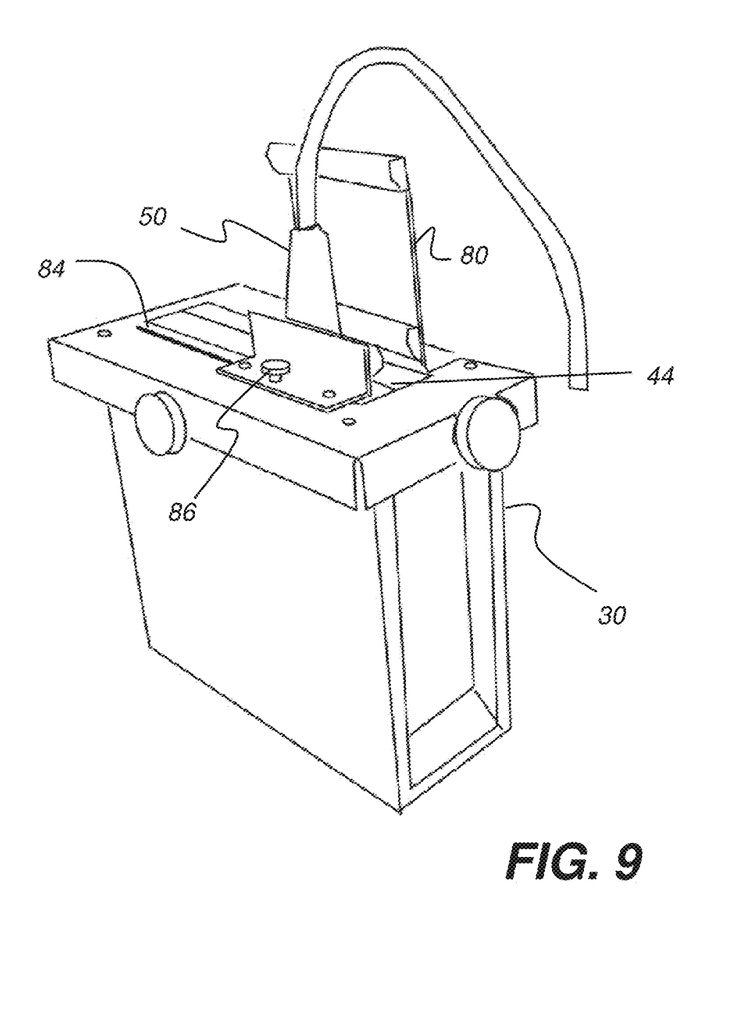
FIG. 9 is a perspective view that shows an embodiment wherein the bracket position is adjustable along the cutout.

FIG. 9 is a perspective view that shows an embodiment wherein the bracket 80 position is adjustable along the cutout 44. Bracket 80 translates along a slot 84 and locks into place with a thumbscrew 86 or other fastener, for example. It can be appreciated that other types of slide or other adjustable feature can be provided for setting the position of bracket 80 or other support feature.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. A fixture for securing a sonography transducer in place against a test surface of a phantom, comprising:

a cap having a cap surface, wherein the cap is configured to seat against an edge of the phantom and maintain spacing between the cap surface and the test surface;

a plurality of discrete, spaced apart cutouts disposed in the cap surface, each of the plurality of cutouts dimensioned to receive a sonography transducer and maintain acoustical contact between the transducer and the test surface only when the transducer is disposed within the cutout; and one or more supports within or adjacent each of the plurality of cutouts stabilizing at least one side of the transducer within the cutout.

2. The fixture of claim 1 further comprising one or more fasteners for coupling the cap against the phantom.

3. The fixture of claim 2 wherein the one or more fasteners are taken from the group consisting of mechanical latches, clips, hinges, magnetic elements, and hook and loop fasteners.

4. The fixture of claim 1 further comprising a bracket that extends outward from the cap for gripping the sonography transducer.

5. The fixture of claim 1 wherein the plurality of cutouts further comprise a slotted diaphragm formed from rubber or plastic.

6. A method for securing a sonography transducer in place against a test surface of a phantom, comprising:

providing a test fixture including a cap having a cap surface and a plurality of discrete, spaced apart cutouts in the cap surface, each of the plurality of cutouts (i) being configured to receive a transducer and (ii) having one or more supports within or adjacent the cutout;

seating the cap surface of the cap against an edge of the test surface of the phantom to maintain a consistent spacing in a horizontal plane between the cap surface and the test surface; and maintaining both a physical and acoustical contact between the transducer and phantom by:

inserting the transducer into, but not through, one of the plurality of cutouts; and stabilizing, in the horizontal plane, at least one side of the transducer within the cutout against the one or more supports of the cutout.

7. The method of claim 6 further comprising fastening the cap to the sonography phantom.

8. The method of claim 6 further comprising fitting the transducer against one or more brackets extending outward from the cap surface.

9. The fixture of claim 1 wherein the plurality of cutouts includes at least two cutouts, each of the cutouts having a different configuration to allow positioning of the transducer at alternate angles.

10. The fixture of claim 1 wherein the plurality of cutouts includes at least two cutouts, each of the cutouts having a different size to accommodate different transducers.

11. The fixture of claim 1 wherein the plurality of cutouts includes at least two cutouts, each of the cutouts being disposed at different locations such that the transducer can be moved to different portions of the phantom to obtain signals from alternative positions.

* * * * *